United States Patent
Ying et al.

(10) Patent No.: US 6,245,401 B1
(45) Date of Patent: Jun. 12, 2001

(54) SEGMENTED CONFORMABLE BREATHABLE FILMS

(75) Inventors: Sandy Chi-Ching Ying, Alpharetta; Lavada Campbell Boggs, Marietta, both of GA (US); Kevin George Hetzler, Sparta, NJ (US); Glen Thomas Mildenhall, Marietta, GA (US); Michael Tod Morman, Alpharetta, GA (US); Dan Kenneth Schiffer, Marietta, GA (US); Susan Elaine Shawver, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/267,412

(22) Filed: Mar. 12, 1999

(51) Int. Cl.$^7$ ............... B32B 3/00; B32B 7/02; B32B 3/26

(52) U.S. Cl. ............ 428/58; 428/212; 428/218; 428/315.5

(58) Field of Search .............. 418/212, 53, 58, 418/40.1, 155

(56) References Cited

U.S. PATENT DOCUMENTS

| | | | |
|---|---|---|---|
| 2,342,150 | 2/1944 | Kleinicke | 252/354 |
| 2,969,332 | 1/1961 | Lawler et al. | 252/354 |
| 3,167,514 | 1/1965 | Baker | 252/170 |
| 3,397,428 | 8/1968 | Donald | 18/13 |
| 3,398,431 | 8/1968 | Corbett | 18/13 |
| 3,448,183 | 6/1969 | Chisholm | 264/37 |
| 3,562,042 | 2/1971 | Zizlsperger et al. | 156/78 |
| 3,575,782 | 4/1971 | Hansen | 161/141 |
| 3,756,758 | 9/1973 | Prall | 425/197 |
| 3,800,796 | 4/1974 | Jacob | 128/284 |
| 3,883,279 | 5/1975 | Heyer | 425/141 |
| 3,920,365 | 11/1975 | Mules | 425/141 |
| 4,197,069 | 4/1980 | Cloeren | 425/131.1 |
| 4,205,679 | 6/1980 | Repke et al. | 128/287 |
| 4,285,100 | 8/1981 | Schwarz | 19/161.1 |
| 4,307,143 | 12/1981 | Meitner | 252/91 |
| 4,368,565 | 1/1983 | Schwarz | 26/99 |
| 4,434,087 | 2/1984 | Hampson et al. | 252/545 |
| 4,492,549 | 1/1985 | Rasmussen et al. | 425/131.1 |
| 4,525,407 | 6/1985 | Ness | 428/138 |
| 4,533,510 | 8/1985 | Nissel | 264/171 |
| 4,687,477 | 8/1987 | Suzuki et al. | 604/385 |
| 4,701,171 | 10/1987 | Boland et al. | 604/385 |
| 4,777,073 | * 10/1988 | Sheth | 428/155 |
| 4,839,098 | 6/1989 | Wisotzki et al. | 252/557 |
| 4,842,596 | 6/1989 | Kielpikowski et al. | 604/385.2 |

(List continued on next page.)

FOREIGN PATENT DOCUMENTS

| | | |
|---|---|---|
| 0 806 196 | 11/1997 | (EP) . |
| 2311249 | * 9/1997 | (GB) ............ C09J/123/00 |
| 95/16562 | 6/1995 | (WO) . |
| 95/17302 | 6/1995 | (WO) . |

OTHER PUBLICATIONS

Abstract of Japanese 40–1192860.
EDI Ployside® Brochure (Date unknown).

Primary Examiner—Blaine Copenheaver
Assistant Examiner—Christopher C. Pratt
(74) Attorney, Agent, or Firm—Ralph H. Dean, Jr.; Douglas H. Tulley, Jr.

(57) ABSTRACT

Unitary films are provided having at least first and second film segments which extend adjacent one another and are permanently joined together. The first and second segments have different compositions whereby the unitary film includes distinct segments having varied physical properties such as, for example, varied levels of high water-vapor transmission rates and/or elasticity. The unitary films and laminates thereof are well suited for use as outer covers in personal care articles and various other barrier articles.

36 Claims, 5 Drawing Sheets

U.S. PATENT DOCUMENTS

| | | | |
|---|---|---|---|
| 4,842,666 | 6/1989 | Werenicz | 156/161 |
| 4,846,658 | 7/1989 | McMullen | 425/197 |
| 4,892,784 | 1/1990 | Reeves et al. | 428/288 |
| 4,906,513 | 3/1990 | Kebbell et al. | 428/198 |
| 4,938,888 | 7/1990 | Kiefer et al. | 252/91 |
| 4,940,626 | 7/1990 | Rhodes, III et al. | 428/198 |
| 4,963,428 | 10/1990 | Harvey et al. | 428/220 |
| 4,984,584 | 1/1991 | Hansen et al. | 128/898 |
| 5,011,698 | 4/1991 | Antoon, Jr. et al. | 426/395 |
| 5,015,414 | 5/1991 | Kamegai et al. | 252/545 |
| 5,041,275 | 8/1991 | Miller | 423/269 |
| 5,094,770 | 3/1992 | Sheridan et al. | 252/91 |
| 5,120,484 | 6/1992 | Cloeren | 264/171 |
| 5,120,594 | 6/1992 | Mrozinski | 428/195 |
| 5,200,443 | 4/1993 | Hudson | 524/99 |
| 5,232,777 | 8/1997 | Sipinen et al. | 428/364 |
| 5,279,677 | 1/1994 | Das | 134/3 |
| 5,312,576 | 5/1994 | Swei et al. | 264/112 |
| 5,342,469 | 8/1994 | Boford et al. | 156/244.22 |
| 5,370,816 | 12/1994 | Balzer et al. | 252/132 |
| 5,382,400 | 1/1995 | Pike et al. | 264/168 |
| 5,385,750 | 1/1995 | Aleksejczyk et al. | 427/4 |
| 5,385,775 | 1/1995 | Wright | 428/284 |
| 5,431,644 | 7/1995 | Sipinen et al. | 604/385.2 |
| 5,440,764 | 8/1995 | Matsushita | 2/401 |
| 5,460,861 | 10/1995 | Vicik et al. | 428/34.9 |
| 5,468,428 | 11/1995 | Hanschen et al. | 264/483 |
| 5,472,775 | 12/1995 | Obijeski et al. | 428/220 |
| 5,506,049 | 4/1996 | Swei et al. | 428/323 |
| 5,507,736 | 4/1996 | Clear et al. | 604/385.2 |
| 5,527,304 | 6/1996 | Buell et al. | 604/385.2 |
| 5,569,232 | 10/1996 | Roe et al. | 604/385.2 |
| 5,575,874 | 11/1996 | Griesbach, III et al. | 156/167 |
| 5,582,903 | 12/1996 | Levy et al. | 428/219 |
| 5,605,749 | 2/1997 | Pike et al. | 442/60 |
| 5,614,297 | 3/1997 | Velazquez | 428/218 |
| 5,616,385 * | 4/1997 | Rothrum et al. | 428/40.1 |
| 5,620,788 | 4/1997 | Garavaglia et al. | 442/118 |
| 5,634,216 | 6/1997 | Wu | 2/239 |
| 5,650,214 | 7/1997 | Anderson et al. | 428/152 |
| 5,650,223 | 7/1997 | Weinberger et al. | 442/62 |
| 5,683,533 | 11/1997 | Keighley et al. | 156/204 |
| 5,691,035 | 11/1997 | Chappell et al. | 428/152 |
| 5,695,868 | 12/1997 | McCormack | 428/283 |
| 5,704,928 | 1/1998 | Morita et al. | 604/385.1 |
| 5,704,930 | 1/1998 | Lavash et al. | 604/385.2 |
| 5,840,412 | 11/1998 | Wood et al. | 428/284 |
| 5,843,066 | 12/1998 | Dobrin | 604/385.1 |
| 5,846,232 | 12/1998 | Serbiak et al. | 604/385.2 |
| 5,865,823 * | 2/1999 | Curro | 604/367 |

* cited by examiner

SEGMENTED CONFORMABLE BREATHABLE FILMS

FIELD OF THE INVENTION

The present invention relates to breathable barriers and more particularly the present invention relates to extensible breathable barrier films and articles incorporating the same.

BACKGROUND OF THE INVENTION

Liquid impervious, vapor permeable films have become an important article of commerce, finding a wide variety of applications including use as outer covers for personal care products (e.g. diapers or incontinence garments), medical garments, industrial workwear and so forth. By providing an article with high breathability (i.e. high vapor permeability) it is possible to provide a body article that is more comfortable to wear since the migration of water vapor through the fabric helps reduce and/or limit discomfort resulting from excess moisture trapped against the skin. In addition, laminates of such films have found use in various bodily articles as well as numerous other applications. The films can provide the desired barrier properties to the article while other materials laminated thereto can provide additional desired characteristics such as strength, abrasion resistance and/or good hand.

While a variety of breathable films and film laminates are known in the art, one particularly useful laminate uses a breathable barrier comprising a stretched filled microporous film. Such films are typically filled with particles or other matter and then crushed or stretched to form a fine pore network throughout the film. The pores result from the separation of the polymer from the filler. The film pore network allows gas and water vapor to pass through the film while acting as a barrier to liquids and particulate matter. The amount of filler within the film and the degree of stretching is controlled so as to create a network of micropores of a size and/or frequency to impart the desired level of breathability to the fabric. An exemplary stretched filled-film is described in commonly assigned U.S. Pat. No. 5,855,999 to McCormack which discloses a filled-film comprising a predominantly linear polyolefin polymer, a bonding agent and about 30% to 80% by weight calcium carbonate, wherein the filled-film can be stretched to impart the desired degree of porosity to the film. The stretched film may then be laminated to a nonwoven web to create a laminate that takes advantage of the strength and integrity of the nonwoven web and the barrier properties of the stretched film.

While providing a more comfortable personal care product from the wearer's perspective, highly breathable liquid-impervious outer covers often suffer from an unwanted and unpleasant outer cover dampness. Continued use of a personal care article after fluid has been discharged and absorbed by the article can cause the outer cover to develop a wet or damp feel. However, this unpleasant wet feeling is not typically due to permeation of liquid through the liquid-impermeable cover or leakage from the article but is simply condensation on the outer cover resulting from the water vapor passing therethrough. Nevertheless, outer cover dampness is desirably limited to the extent possible.

In addition to breathability of the film and film laminates, the ability of the garment or article to exhibit elastic properties allows the garment to provide better body conformance. However, providing a low cost film or film laminate that achieves the desired conformance and breathability has proven difficult, particularly with microporous filled-films.

In order to achieve good body conformance, the polymer composition of the film desirably has good stretch and recovery properties and yet must also be capable of allowing formation and retention of pores within the film. Furthermore, the breathable film laminate must be sufficiently stable so as to maintain the desired characteristics while in use (e.g. at about 37° C. or body temperature) as well as over time and shelf-aging. In this regard, it has been found that such conditions can decrease the breathability and/or reduce the stretch-recovery of the film and/or film laminates.

Thus, there exists a need for films and laminates thereof which are capable of providing good breathability and body conformance. Further, there exists a need for such films and laminates thereof that are sufficiently heat stable to maintain the desired properties when subjected to the conditions commonly experienced in further processing, use, storage and/or transportation. Further, there likewise exists a need for low cost films and film laminates that provide good breathability and body conformance while also providing excellent hand and aesthetic qualities. Still further, there exists a need for absorbent bodily articles which allow sufficient water vapor permeation such that the bodily articles remain comfortable products for the wearer yet which do not allow excessive condensate from water vapor to readily form on the outer cover and create and article having a wet or damp feel.

SUMMARY OF THE INVENTION

The aforesaid needs are fulfilled and the problems experienced by those skilled in the art overcome by the multi-segmented film of the present invention which comprises a unitary film having a first film segment and a second film segment which extend adjacent one another in at least the machine direction and/or cross-machine direction and wherein the first film segment comprises a first thermoplastic polymer and has a WVTR of at least 800 g/m$^2$/24 hours. The second film segment can have a WVTR less than that of the first film segment thereby providing a unitary film having varied regional breathability. As an example, the first film segment can comprise a microporous film. The second film segment can comprise a breathable or non-breathable segment. In a particular aspect, both the first and second film segments can comprise microporous films. In addition, the second film segment can comprise an elastic film segment.

In a further aspect of the present invention, the multi-segment films of the present invention can be laminated or fixedly attached to a sheet such as, for example, a nonwoven web, woven fabric, and so forth. In addition, the films and film laminates of the present invention are well suited for use in personal care articles, protective apparel, protective covers and infection control products. As an example, personal care articles of the present invention can comprise (i) a liquid pervious topsheet; (ii) a liquid impervious outer cover comprising a multi-segmented film or film laminate as described herein; and (iii) an absorbent core positioned between the outer cover and topsheet. The first and second film segments can be selectively positioned within the article to provide the desired attributes such as body conformance, regional water vapor transmission rates and/or aesthetics.

DEFINITIONS

As used herein, the term "comprising" is inclusive or open-ended and does not exclude additional unrecited elements, compositional components, or method steps.

As used herein the term "nonwoven" fabric or web means a web having a structure of individual fibers or threads which are interlaid, but not in an identifiable manner as in a knitted or woven fabric. Nonwoven fabrics or webs have been formed by many processes such as for example, meltblowing processes, spunbonding processes, hydroentangling, air-laid and bonded carded web processes.

As used herein the term "spunbond fibers" refers to small diameter fibers of molecularly oriented polymeric material. Spunbond fibers are generally formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartman, U.S. Pat. No. 3,542,615 to Dobo et al, U.S. Pat. No. 5,382,400 to Pike et al. and in commonly assigned U.S. patent applications Ser. No. 08/756,426 now allowed filed Nov. 26, 1996 to Marmon et al. and U.S. application Ser. No. 08/565,261 now U.S. Pat. No. 5,759,926 filed Nov. 30, 1995 to Pike et al.

As used herein the term "meltblown fibers" means fine fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al.; U.S. Pat. No. 4,526,733 to Lau; U.S. Pat. No. 5,652,048 to Haynes et al.; and U.S. Pat. No. 5,366,793 to Fitts et al. Meltblown fibers may be continuous or discontinuous, are generally less than 10 microns in average diameter, and are commonly between about 0.5 and about 7 microns in average diameter.

As used herein "multilayer nonwoven laminate" means a multilayer laminate comprising at least one layer of a nonwoven web and/or multiple nonwoven layers such as, for example, a spunbond/meltblown/spunbond (SMS) laminate. Examples of multilayer nonwoven laminates are disclosed in U.S. Pat. No. 4,041,203 to Brock et al., U.S. Pat. No. 5,178,931 to Perkins et al. and U.S. Pat. No. 5,188,885 to Timmons et al.

As used herein, the term "sheet" refers to a layer of material which can be a woven material, knitted material, scrim, nonwoven web or other like material.

As used herein, the term "machine direction" or MD means the length of a fabric in the direction in which it is produced. The term "cross machine direction" or CD means the width of fabric, i.e. a direction generally perpendicular to the MD.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein the term "blend" means a mixture of two or more polymers while the term "alloy" means a sub-class of blends wherein the components are immiscible but have been compatibilized.

As used herein, "ultrasonic bonding" means a process performed, for example, by passing the fabric between a sonic horn and anvil roll as illustrated in U.S. Pat. No. 4,374,888 to Bornslaeger.

As used herein "point bonding" means bonding one or more layers of fabric at a plurality of discrete bond points. For example, thermal point bonding generally involves passing one or more layers to be bonded between heated rolls such as, for example an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of thermal point bonding is described in U.S. Pat. No. 3,855,046 to Hansen et al. Numerous other bonding patterns are known such as, for example, those described in U.S. Design Pat. No. 356,688 to Uitenbroek et al. and U.S. Pat. No. 5,620,779 to Levy et al.

As used herein, the term "barrier" means a film, laminate or other fabric which is relatively impermeable to the transmission of liquids and which has a hydrohead of at least about 50 mbar. Hydrohead as used herein refers to a measure of the liquid barrier properties of a fabric measured in millibars (mbar) as described herein below. However, it should be noted that in many applications of barrier fabrics, it may be desirable that they have a hydrohead value greater than about 80 mbar, 150 mbar or even 200 mbar.

As used herein, the term "breathability" refers to the water vapor transmission rate (WVTR) of an area of fabric which is measured in grams of water per square meter per day ($g/m^2/24$ hours). WVTR can be measured as indicated below and the results are reported in grams/square meter/day. Further, as used herein the term "breathable" refers to a fabric having a WVTR of at least 800 $g/m^2/24$ hours.

As used herein, the term "elastic" generally refers to material which, upon application of a biasing force, is extensible or elongatable in at least one direction and returns substantially to its original dimensions immediately after the biasing force is removed.

As used herein, the term "scrim" means a lightweight fabric used as a backing material. Scrims are often used as the base fabric for coated or laminated products. As used herein, the term "garment" means any type of non-medically or non-industrial oriented apparel which may be worn. This includes coveralls, undergarments, pants, shirts, jackets, gloves, socks, and the like.

As used herein, the term "infection control product" means medically oriented items such as surgical gowns and drapes, head coverings like bouffant caps, surgical caps and hoods, industrial workwear, footwear like shoe coverings, boot covers and slippers, wound dressings, bandages, sterilization wraps, lab coats, coveralls, aprons and so forth.

As used herein, the term "protective apparel" means industrial related apparel or garments such as coveralls, aprons, workwear, coveralls and so forth.

As used herein, the term "personal care product" means personal hygiene oriented items such as diapers, training pants, absorbent underpants, adult incontinence products, feminine hygiene products, and the like.

As used herein, the term "protective cover" means a cover for vehicles such as cars, boats, airplanes, etc., covers for articles or equipment often left outdoors (e.g. grills and lawn furniture), yard and garden equipment, floor coverings, tents and the like.

DESCRIPTION OF THE INVENTION

Multi-segmented films of the present invention comprise two or more segments wherein at least one segment is breathable. In reference to FIGS. 1 and 1A, a multi-segmented film 10 is shown having first segments 12 and a second segments 14 wherein at least first segments 12 are breathable. As used herein, the term "breathable" refers to a material which is permeable to water vapor having a minimum WVTR of about 800 $g/m^2/24$ hours. Desirably, first segments 12 comprise at least about 5% of the area of multi-segmented film 10 and, even more desirably, comprise between about 25% and about 95% of the area of multi-segmented film 10. The multi-segmented film 10 desirably has a hydrohead value of at least about 50 millibars and still more desirably has a hydrohead value in excess of about 75 millibars. In addition, although thicker multi-segmented films are possible, the unitary multi-segmented film preferably has a maximum film thickness less than about $50\mu$ (microns) and still more desirably has a maximum film thickness between about $10\mu$ and about $35\mu$. The first and second segments 12 and 14 can be selected to comprise distinct films having varied attributes such as, for example, distinct WVTR and/or elastic properties.

Multi-segmented films, as described herein, having distinct film segments which exhibit varied levels of breathability and/or elasticity can be formed by various methods. Multi-segmented films can be formed by coextruding the respective adjacent segments such as, for example, using the method and apparatus for forming films as disclosed in U.S. Pat. No. 4,533,510 to Nissel et al., the entire contents of which are incorporated herein by reference. Film dies for forming side-by-side coextruded films are commercially available from Extrusion Dies, Inc. of Chippewa Falls, Wis. The desired components of the respective film segments can be separately mixed, heated and then coextruded into the respective side-by-side segments of a unitary multi-segmented film. The film may be made by any one of a variety of film forming processes known in the art such as, for example, by using either cast or blown film equipment. The extruded multi-segmented film is then processed as desired. In a further aspect, the individual film segments of the unitary film can be separately produced and subsequently attached to one another. As an example, the films comprising the respective segments can be produced and positioned such that the edges of the respective films overlap. The film segments can then be bonded to one another along the overlapping interface by thermal, ultrasonic or adhesively bonding the same. Desirably the overlapping portions of the films are permanently welded together utilizing a combination of heat and pressure.

In one aspect, the unitary multi-segmented film can be stretched in at least one direction, thereby reducing the film gauge or thickness. As discussed in more detail herein below, a particularly desirable film is a microporous stretched filled-film and such films include at least a thermoplastic polymer and filler. With regard to microporous stretched filled-films, in addition to reducing the film thickness stretching also imparts porosity to the film and forms a micropore network therein which renders the films breathable. As used herein a "filler" is meant to include particulates and other forms of materials which can be added to the polymer and which will not chemically interfere with or adversely affect the extruded film but is able to be dispersed throughout the film. The filler particles may optionally be coated with a fatty acid, such as stearic acid or behenic acid, and/or other material in order to facilitate the free flow of the particles (in bulk) and their ease of dispersion into the polymer. Stretching can be achieved by various means known to those skilled in the art. Films can be stretched or oriented in either or both the MD and CD. As examples, machine direction orientation equipment is commercially available from vendors such as the Marshall and Williams Company of Providence, R.I. and biaxial orientation equipment is commercially available from Bruckner GMBH of Siegsdorf, Germany. As a further example, the films can be stretched utilizing grooved or patterned rollers such as, for example, those described in U.S. Pat. No. 4,153,751 to Schwarz, U.S. Pat. No. 5,028,289 to Rasmussen and commonly assigned U.S. patent application Ser. No. 60/108,773 filed Nov. 17, 1998 to Jameson et al.; the entire contents of the aforesaid references are incorporated herein by reference. When using one or more elastic segments it may be advantageous to anneal or heat set the stretched multi-segmented film while in the stretched or tensioned state in order to set the elastic segment and reduce the potential for puckering of the film caused by the retractive force of the elastic segments. In addition, when using films which have been independently pre-formed and subsequently joined, it is possible to process the films, for example to stretch-thin the films and so forth, either prior to or after permanently joining the respective segments together to form a unitary multi-segmented film.

There exist a wide variety of polymers suitable for use with the present invention. The multi-segmented film can be made from any thermoplastic polymer suitable for film formation and desirably comprise thermoplastic polymers which can be readily stretched to reduce the film gauge or thickness. Film forming polymers suitable for use with the present invention, alone or in combination with other polymers, include, by way of example only, polyolefins, ethylene vinyl acetate (EVA), ethylene ethyl acrylate (EEA), ethylene acrylic acid (EAA), ethylene methyl acrylate (EMA), ethylene normal butyl acrylate (EnBA), polyester, polyethylene terephthalate (PET), nylon, ethylene vinyl alcohol (EVOH), polystyrene (PS), polyurethane (PU), polybutylene (PB), polyether esters, polyether amides, and polybutylene terephthalate (PBT).

Preferred polymers for forming one or more of the film segments, include, but are not limited to, polyolefins. A wide variety of polyolefin polymers exist and the particular composition of the polyolefin polymer and/or method of making the same is not believed critical to the present invention and thus both conventional and non-conventional polyolefins capable of forming films are believed suitable for use in the present invention. As used herein, "conventional" polyolefins refers to those made by traditional catalysts such as, for example, Ziegler-Natta catalysts. Suitable polyethylene and polypropylene polymers are widely available and, as one example, linear low density polyethylene is available from the Dow Chemical Co. under the trade name AFFINITY or ASPUN and conventional polypropylene is available from Exxon Chemical Company under the trade name ESCORENE. In addition, elastic and inelastic polyolefins made by "metallocene", "constrained geometry" or "single-site" catalysts are also suitable for use in the present invention. Examples of such catalysts and polymers are described in U.S. Pat. No. 5,472,775 to Obijeski et al.; U.S. Pat. No. 5,451,450 to Erderly et al.; U.S. Pat. No. 5,278,272 to Lai et al.; U.S. Pat. No. 5,272,236 to Lai et al.; U.S. Pat. No. 5,204,429 to Kaminsky et al.; U.S. Pat. No. 5,539,124 to Etherton et al.; and U.S. Pat. No. 5,554,775 to Krishnamurti et al.; the entire contents of which are incorporated herein by reference. The aforesaid patents to Obijeski and Lai teach exemplary polyolefin elastomers and, in addition, exemplary low density polyethylene elastomers are commercially available from Dow Chemical Company of Midland, Mich. under the trade name AFFINITY, from Exxon Chemical Co. of Houston, Tex., under the trade name EXACT, and from Dupont Dow Elastomers, L.L.C. under the trade name ENGAGE.

In addition, stereoblock polymers are also believed well suited for practicing the present invention. The term "stereoblock polymer" refers to polymeric materials with controlled regional tacticity or stereosequencing to achieve desired polymer crystallinity. By controlling the stereoregularity during polymerization, it is possible to achieve atacticisotactic stereo blocks. Methods of forming polyolefin stereoblock polymers are known in the art and are described in the following articles: G. Coates and R. Waymouth, "Oscillating Stereocontrol: A Strategy for the Synthesis of Thermoplastic Elastomeric Polypropylene" 267 Science 217–219 (January 1995); K. Wagener, "Oscillating Catalysts: A New Twist for Plastics" 267 Science 191 (January 1995). Stereoblock polymers and methods of their production are also described in U.S. Pat. No. 5,594,080 to Waymouth et al., U.S. Pat. No. 5,208,304 to Waymouth and European Patent Application Publication No. 0475306 A1. As indicated above, by controlling the crystallinity of olefins it is possible to provide polymers exhibiting unique tensile modulus and/or elongation properties. In addition, polyolefin copolymers, and in particular propylene-ethylene copolymers, are also suitable for use with the present invention. As but one example, exemplary propylene-ethylene copolymers can comprise multi-step reactor products wherein an amorphous ethylene propylene random copolymer is molecularly dispersed in a predominately semi-crystalline high propylene monomer/low ethylene monomer continuous matrix. Examples of such polymers are described in U.S. Pat. No. 5,300,365 to Ogale; U.S. Pat. No. 5,212,246 to Ogale and U.S. Pat. No. 5,331,047 to Giacobbe. Such polymers are commercially available from Himont, Inc. under the trade name CATALLOY polymers.

Other exemplary commercially available elastomeric materials include, but are not limited to, the following polymers: elastomeric polyurethanes such as, for example, those available under the trade name ESTANE from B.F. Goodrich & Co. or MORTHANE from Morton Thiokol Corp.; elastomeric polyether esters such as, for example, those available under the trade name HYTREL from E. I. DuPont De Nemours & Company, and those available under the trade name ARNITEL available from DSM of Sittard, Holland (formerly available from Akzo Plastics of Arnhem, Holland); and elastomeric polyether amides commercially available from Elf Atochem of Philadelphia, Pa. under the trade name PEBAX. As additional examples, suitable thermoplastic elastomers also include those made from block copolymers having the general formula A-B-A' where A and A' are each a thermoplastic polymer endblock which contains a styrenic moiety such as a poly(vinyl arene) and where B is an elastomeric polymer midblock such as a conjugated diene or a lower alkene polymer. Further, exemplary block copolymers include A-B-A-B tetrablock polymers having an isoprene monomer unit hydrogenated to a substantially poly(ethylene-propylene) monomer unit such as a styrene-poly(ethylene-propylene)-styrene-poly(ethylene-propylene) elastomeric block copolymer. As specific examples, exemplary elastomers can comprise (polystyrene/poly(ethylene-butylene)/polystyrene) block copolymers available from the Shell Chemical Company under the trade name KRATON as well as polyolefin/KRATON blends such as those described in U.S. Pat. No. 4,663,220 to Wisneski et al. and U.S. Pat. No. 5,332,613 to Taylor et al., the entire contents of the aforesaid references are incorporated herein by reference.

As indicated above, the first segment of the multi-segmented film comprises a breathable film. Various breathable films are suitable for use with the present invention, including both microporous and monolithic (i.e. non-porous) films. Breathable films comprising the first segment or segments can be elastic or inelastic and desirably have a WVTR of at least about 800 $g/m^2/day$, and more desirably having a WVTR in excess of about 1500 $g/m^2/day$, and still more desirably a WVTR in excess of about 3500 $g/m^2/day$, and even more desirably a WVTR of about 5000 g/m²/day or more. In one aspect, the first segments can be inelastic or less-elastic than the second segment and exhibit higher breathability levels relative to the second segments. Monolithic or non-microporous breathable films can exhibit good breathability when they comprise polymers which inherently have good water vapor transmission rates (i.e., polymers which allow water vapor to readily diffuse through the film) such as, for example, polyurethanes, polyether esters, polyether amides, EMA, EEA, EVA and the like. Examples of breathable microporous films suitable for use as one or more segments of the multi-segmented film include, but are not limited to, those described in the following references: U.S. Pat, No. 5,695,868 to McCormack; U.S. Pat. No. 6,075,179 to McCormack et al.; U.S. patent application Ser. No. 08/722,726 filed Oct. 1, 1996 to McCormack et al.; U.S. patent application Ser. No. 08/882,712 filed Jun. 25, 1997 to McCormack et al.; U.S. Pat. No. 6,111,163 to McCormack et al.; U.S. Pat. No. 6,045,900 to Haffner et al.; U.S. patent application Ser. No. 08/843,147 filed Apr. 25, 1997 to Gwaltney et al; and U.S. patent application Ser. No. 09/122,326 filed Jul. 24, 1998 to Shawver et al; U.S. Pat. No. 4,777,073 to Sheth; and U.S. Pat. No. 4,867,881 to Kinzer; the entire contents of the aforesaid references are incorporated herein by reference.

The second segments can be non-breathable or breathable film segments and, desirably, comprise breathable films. In addition, the second segments can be elastic or inelastic films. Desirably the second segments are elastic films and comprise one or more elastic polymers. The second segments can comprise films similar to those described above with respect to the first segments. However, the composition and/or structure of the first segment is distinct from that of the second segment and the specific composition and/or structure of the first and second segments will be selected with respect to one another to achieve the desired functional and/or aesthetic attributes of the unitary, multi-segmented film. The particular film composition and/or structure of the respective segments can be selected with respect to various considerations such as end use, cost, durability, strength, shelf and product life expectancy, etc. Various examples of which are discussed in more detail herein and throughout.

In one aspect of the invention, a multi-segmented film can comprise a film having varied regional breathability. As an example, still in reference to FIGS. 1 and 1A, first segments 12 can comprise breathable films separated along a length of the film by second segments 14. Second segments 14 can comprise either breathable or non-breathable films. In order to achieve a unitary film having varied regional breathability first segments 12 can be selected to have a higher WVTR relative to second segments 14. WVTRs of adjacent segments can vary in accord with the selected film composition and/or structure thereof, thereby yielding a film having adjacent segments with distinct levels of breathability. In this regard, first and second segments 12 and 14 can have distinct WVTRs by selecting different film compositions for the respective segments. As an example, first segments 12 can have a higher weight percent of filler than second segments 14. Thus, stretching of the filled film creates a multi-segmented film 10 having first breathable segments 12 and second breathable segments 14 wherein the WVTR of first segments 12 are higher than the WVTR of second segments 14. Additionally and/or alternatively, first and second segments 12 and 14 can comprise different types of filler materials. The WVTRs of the respective segments can thus be varied in accord with the desired application of the multi-segmented film. High and low breathability segments can be strategically located within the unitary multi-segmented film to achieve the desired breathability levels in selected locations.

Figure 1:
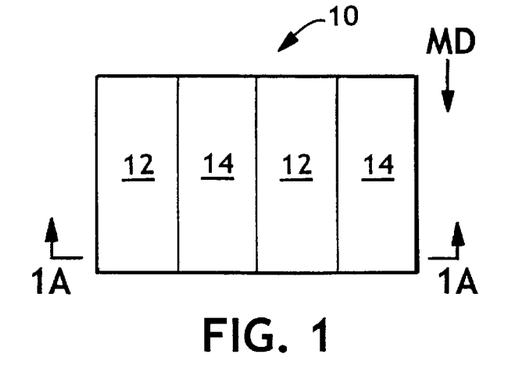
FIG. 1 is a top, plan view of a multi-segmented film of the present invention.
Figure 1A:
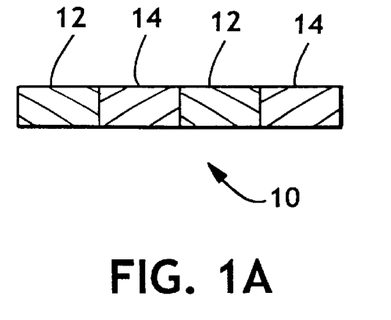
FIG. 1A is a cross-sectional view of the multi-segmented film of FIG. 1 taken at 1A—1A.

In a further aspect, it may be desirable to have each of the segments comprise an opaque film. This may be aesthetically desirably in certain articles, such as diapers, to mask a soiled absorbent core. Opacifying fillers can be included within one or more of the segments as needed in order to create a multi-segmented film which is uniformly opaque. However, the weight percent and/or type of filler can be varied amongst respective segments in order to selectively achieve disparate breathability levels while having substantially uniform opacity. As a specific example, first segments 12 can comprise a highly breathable microporous LLDPE film having $CaCO_3$ filler particles and second segments 14 can comprise a less breathable and less porous LLDPE film having $TiO_2$ filler particles.

As a further example, first and second segments 12 and 14 can comprise different polymers in order to achieve distinct WVTR levels. In this regard, the respective segments can comprise either microporous or non-microporous films and/ or filled or unfilled films utilizing different polymeric compositions. In one aspect, first segments 12 can comprise a filled polymeric film and second segments 14 a filled polymeric film comprising a polymer different from that comprising first segments 12, wherein upon stretching of the unitary multi-segmented film 10 a higher level of breathability is imparted to first segments 12 relative to the WVTR of the second segments 14. As an example, first segments 12 can comprise a linear low density polyethylene (LLDPE) filled film and second segments 14 can comprise an elastomeric polyethylene filled film. The resulting breathable stretched-thinned film will have first segments 12 with a higher WVTR than second segments 14. The amount and/or type of filler can likewise be varied in combination with polymer composition in order to achieve the desired WVTR, opacity and/or elasticity within the respective segments.

In a further aspect, unitary films with improved body conformance can also be achieved in accord with the present invention. Still in reference to FIGS. 1 and 1A, multi-segmented film 10 can comprise first and second segments 12 and 14 wherein one of the first or second segments are elastic and the other segments are breathable segments. As an example, first segments 12 can comprise inelastic breathable segments whereas second segments 14 can comprise an elastic segment. Desirably, first breathable segments 12 comprise at least about 25% of the area of multi-segmented film 10 and, even more desirably, comprise between about 50% and about 95% of the area of multi-segmented film 10. The elastic, second segments 14 can comprise a breathable or a non-breathable film. As a particular example, first segments 12 can comprise a microporous LLDPE filled film and second segments 14 a non-porous film comprising an elastomeric polyolefin such as elastomeric polyethylene. Alternatively, second segments can comprise an elastic breathable non-porous film such as, for example, a polyurethane, polyether ester, or polyether amide film. Still further, the first segment can comprise a microporous polyolefin filled-film and the second segment can comprise a KRATON/polyolefin polymer blend.

Elastic film segments can comprise an elastomer and desirably have a hysteresis of less than 60% and more desirably a hysteresis of less than about 50% and still more desirably a hysteresis of less than about 40%. Inelastic segments can include those segments comprising a non-elastomeric polymer having a hysteresis of greater than about 60%. In a further aspect the elastic film segments can comprise a film of a thermoplastic elastomer having a retraction/extension percent greater than 25 and desirably has a retraction/extension percent greater than about 35 and still more desirably a retraction/extension percent of at least about 50. In this regard, inelastic film segments can comprise a film of a thermoplastic polymer having retraction/extension ratio less than about 25. In a further aspect, the elastic segments desirably comprise a thermoplastic elastomer film which, upon application of a biasing force, is elongatable, to a stretched or biased length which is at least about 160 percent of its relaxed unbiased length, and which, will immediately recover at least 55 percent of its elongation upon release of the elongating force. A hypothetical example would be a one (1) centimeter sample of a material which is elongatable to at least 1.60 centimeters and which, upon release of the elongating force, will recover to a length of not more than 1.27 centimeters. Many thermoplastic elastomer films exhibit greater stretch and recovery properties and many highly elastic materials can be stretched to 160 percent of their relaxed unbiased length, and immediately recover in excess of about 75% percent of its elongation upon release of the elongating force.

Figure 2:
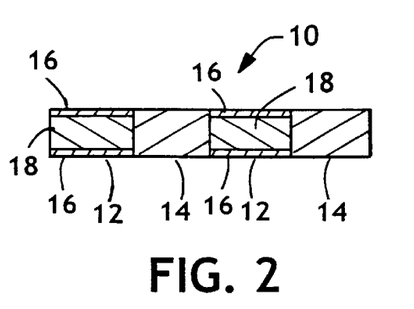
FIG. 2 is a cross-sectional view of a multi-segmented film of the present invention.
Figure 3:
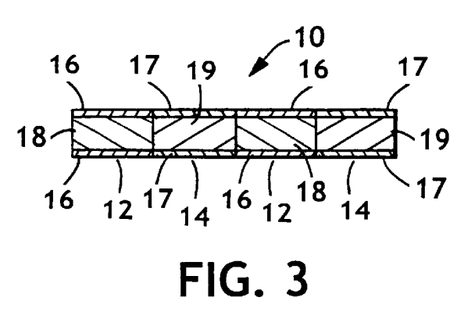
FIG. 3 is a cross-sectional view of a multi-segmented film of the present invention.

In a further aspect of the present invention, the individual film segments may themselves comprise either mono-layer or multi-layered films. In reference to FIG. 2, a multi-segmented film 10 is shown wherein first segments 12 comprises a multi-layered film and second segments 14 comprises a mono-layer film. First segments 12 can comprise one or more outer layers 16 and one or more central or intermediate layers 18. In a preferred embodiment multi-layered film segments can comprise films such as, for example, those described in U.S. Pat. No. 6,075,179 to McCormack et al.; U.S. Pat. No. 6,045,900 to Haffner et al. and U.S. patent application No. 08/882,712 filed Jun. 25, 1997 to McCormack et al., the contents of the aforesaid references are incorporated herein by reference. Additionally, first and second segments 12 and 14 can both comprise multi-layered films. In reference to FIG. 3, first segments 12 can comprise outer layers 16 and core layer 18 and second segments 14 can comprise outer layers 17 and core layer 19. Outer layers 16 and 17 of first and second segments 12 and 14 can comprise identical, similar or different compositions. Desirably, however, outer layers 16 and 17 of first and second segments 12 and 14 comprise identical or substantially similar polymer compositions. Where one or more of the segments are elastic it is desirable that outer layers extending over the elastic segments comprise an extensible layer. In this regard, when comprising a small percent of the overall film thickness, layers which by themselves are inelastic can still be utilized as they will not impede the stretch and recovery provided by the elastic core layer. Preferably, however, outer layers extending over elastic segments exhibit good extensibility. As an example, core layer 18 of first segment 12 can comprise an inelastic breathable microporous LLDPE filled film and core layer 19 of second segment can comprise an elastic polyolefin and outer layers 16 and 17 of first and second segments 12 and 14 can comprise a blend of LLDPE and EMA.

Figure 4:
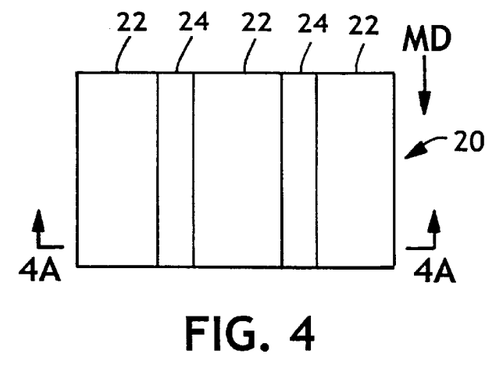
FIG. 4 is a top, plan view of a multi-segmented film of the present invention.
Figure 4A:
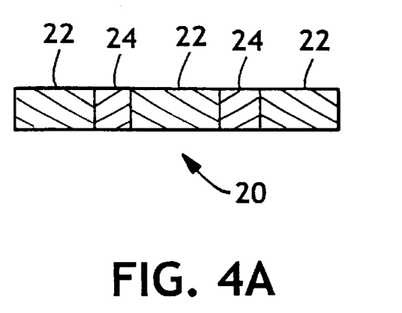
FIG. 4A is a cross-sectional view of the multi-segmented film of FIG. 4 taken at 4A—4A.
Figure 5:
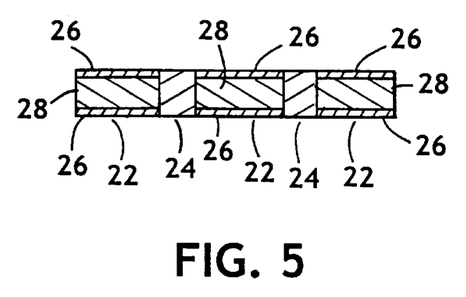
FIG. 5 is a cross-sectional view of a multi-segmented film of the present invention.
Figure 6:
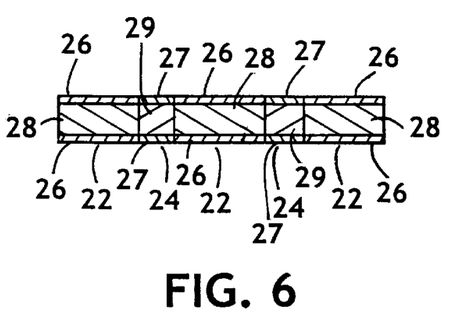
FIG. 6 is a cross-sectional view of a multi-segmented film of the present invention.

In a further aspect of the invention, the multi-segmented film can comprise one or more discrete elastic segments positioned between breathable segments. In one embodiment, the breathable segments comprise substantially inelastic segments having high levels of breathability. In reference to FIGS. 4 and 4A, multi-segmented film 20 can comprise first segments 22 and discrete second segments 24 disposed there between. Discrete elastic segments 24 can either be breathable or non-breathable. Desirably, first breathable segments 22 comprise at least about 25% of the area of multi-segmented film 20 and, even more desirably, comprise between about 50% and about 95% of the area of multi-segmented film 10. In addition, discrete elastic segments have a width (dimension in the CD of the film) of at least 0.1 cm and desirably have a width of at least about 1 cm or more. The width of the breathable segments separating the second elastic segments can vary in accord with the desired attributes of the multi-segmented film; use of larger elastic segments and/or more closely grouped segments will improve the overall stretch and recovery attributes of the unitary multi-segmented film. First breathable segments 22 and second elastic segments 24 can comprise either mono-layer or multi-layer films. In reference to FIG. 5, first breathable segments can comprise a multi-layered film comprising outer layers 26 and a central core layer 28 and second elastic segments 24 can comprise a mono-layer film. In a particular embodiment, first breathable segments 22 can comprise an inelastic multilayered film such as those described in U.S. patent application Ser. No. 08/882,712 filed Jun. 25, 1997 to McCormack et al. and second elastic layers 24 can comprise an elastic polyethylene. As a further example and in reference to FIG. 6, first breathable segments 22 and second elastic segments 24 can both comprise multi-layered films with the first segment comprising outer layers 26 and intermediate layer 28 and second segment comprising outer layers 27 and intermediate layer 29. Desirably, outer layers 26 and 27 of first breathable segments 22 and second elastic segments 24 can comprise a similar or identical polymer composition such as, for example, EMA, EEA, EVA or polyolefin blends thereof.

Figure 7:
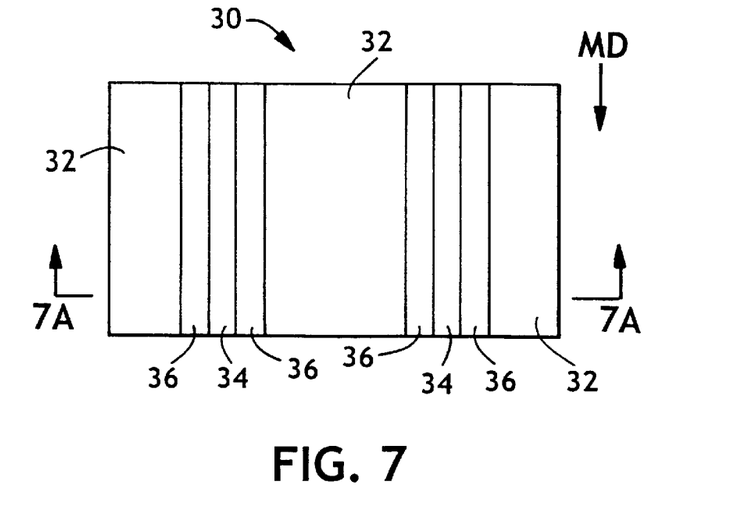
FIG. 7 is a top, plan view of a multi-segmented film of the present invention.
Figure 7A:
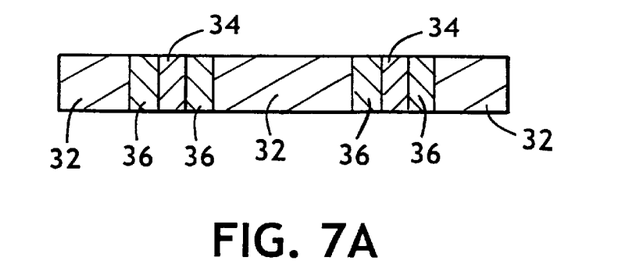
FIG. 7A is a cross-sectional view of the multi-segmented film of FIG. 7 taken at 7A—7A.

As indicated above, a wide variety of polymers are suitable for use with the present invention. Polymers of adjacent segments should be compatible in the sense that they exhibit sufficient cohesion to form a continuous, cohesive film. In this regard, utilization of polymer blends can improve cohesion of adjacent segments. For example, polyethylene and polypropylene are not, by themselves, compatible whereas polyethylene/polypropylene blends can be compatible with polyethylene and/or polypropylene segments. In a particular embodiment, a first segment can comprise LLDPE and a polypropylene impact copolymer (such as taught in U.S. Pat. No. 6,072,005 Kobylivker et al., the entire contents of which are incorporated herein by reference), and an adjacent second segment can comprise an elastic polypropylene. Further, compatibilization may likewise be achieved through addition of one or more bonding or tackifying resins within a segment. Exemplary bonding or tackifying resins are described in U.S. Pat. No. 5,695,868 to McCormack. In addition, compatibilization segments or tie segments can be used in order to utilize a wider range of polymers. Accordingly, the use of a compatibilizing segment makes it possible to achieve a continuous cohesive multi-segmented film using discrete segments of incompatible polymers. In reference to FIG. 7, multi-segmented film 30 can comprise first segments 32 and second segments 34 wherein compatibilizing segments 36 are disposed between first and second segments 32, 34. As a particular example, first segments can comprise a breathable inelastic segment comprising a microporous LLDPE film and second segments can comprise elastic polypropylene. Compatibilizing segments are disposed between the first and second segments and can comprise, for example, an ethylene-propylene copolymer. In a further aspect, a compatibilizing segment can itself comprise a bonding or tackifying resin such as an EASTMAN 1023PL resin which is an amorphous polypropylene tackifying agent available from Eastman Chemical Company Longview, Tex. or amorphous polyalphaolefins such as REXTAC from Huntsman Corporation of Salt Lake City, Utah and VESTOPLAST from Hüls AG of Marl, Germany. Composition of the compatibilizing layer can vary in accord with the desired film attributes and the particular polymers comprising adjacent segments.

Figure 8:
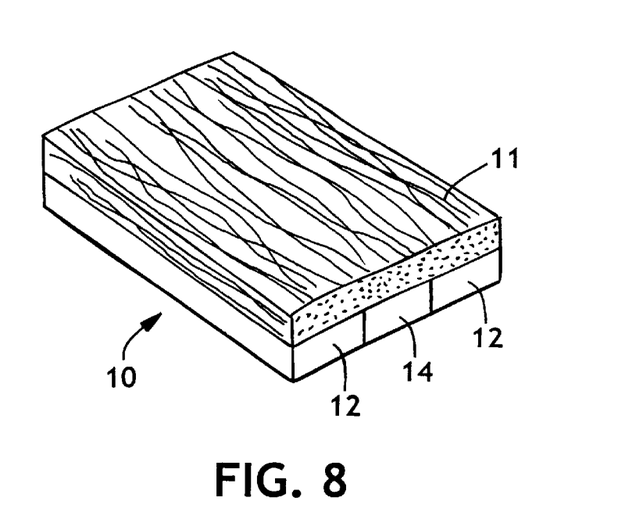
FIG. 8 is a perspective view of a multi-segmented film laminate of the present invention.

The multi-segmented films of the present invention can, optionally, be laminated to one or more additional films and/or fabrics. In reference to FIG. 8, multi-segmented film 10 is bonded to nonwoven web 11. The particular composition of any additional layers attached to the multi-segmented film may be selected to achieve desired attributes such as, for example, aesthetics, strength, durability, hand, etc. As examples, multi-segmented films can be laminated to knitted fabrics, nonwoven fabrics, foams, scrims, multilayered nonwoven laminates, and so forth. The multi-segmented film and other fabric(s) can be laminated together by means known to those skilled in the art such as, for example, by thermal bonding, ultrasonic bonding, adhesive bonding and the like. Thermal point bonding is an exemplary means of laminating the respective layers. Where one or more of the segments within the multi-segmented film comprises an elastic segment, any additional layers laminated thereto desirably comprise an extensible material or fabric. In this regard, the additional layer or layers can comprise, as examples, extensible nonwoven materials (e.g. creped nonwovens or nonwovens comprising highly crimped fibers), meshed fabrics, loosely woven fabrics, elastic composite materials and/or other like materials. Desirably the fabric comprises one or more layers of thermoplastic fibers which are elastic, inherently extensible or which have been treated so as to be become extensible and/or elastic and which also have a cloth-like hand and drape. Examples of suitable extensible and/or elastic materials are described in U.S. Pat. No. 4,965,122 to Morman et al.; U.S. Pat. No. U.S. Pat. No. 5,114,781 to Morman et al.; U.S. Pat. No. 5,336,545 to Morman et al.; U.S. Pat. No. 4,720,415 to Vander Wielen et al.; U.S. Pat. No. 4,789,699 to Kieffer et al.; U.S. Pat. No. 5,332,613 to Taylor et al.; U.S. Pat. No. 5,288,791 to Collier et al.; U.S. Pat. No. 4,663,220 to Wisneski et al.; U.S. Pat. No. 5,540,976 to Shawver et al.; European Application No. 0,712,892 A1 to Djiaw et al.; U.S. Pat. No. 5,952,252 to Shawver et al.; U.S. Pat. No. 5,714,107 to Levy et al.; and U.S. Pat. No. 6,054,002 to Griesbach et al.; the contents of the aforesaid references are incorporated herein by reference. The composition of the thermoplastic polymer may be selected as desired to achieve a material having the desired physical attributes such as, for example, elasticity, hand, tensile strength, cost and so forth. Further, the outer nonwoven layer may be treated such as, for example, by embossing, hydroentangling, mechanically softening, printing, anti-static treatment or treated in some other manner in order to achieve desired aesthetics and/or functional characteristics.

The multi-segmented films of the present invention, and laminates thereof, can be utilized in a wide variety of applications such as, for example, in personal care articles, infection control products, protective apparel, protective covers, garments and so forth. However, it will be appreciated by those skilled in the art that the multi-segmented films of the present invention can be advantageously utilized in numerous other applications employing breathable barrier fabrics. As a particular example, multi-segmented films of the present invention can be readily converted and incorporated within a breathable barrier of a diaper or incontinence garment. Although the breathability provided by microporous films and/or laminates thereof is advantageous in many articles, there exist some situations where high breathability can be undesirable. For example, in personal care articles such as diapers or incontinence garments the breathable barrier and absorbent core generally work together to retain bodily fluids discharged into the garment. However, when fluid is retained within the absorbent core significantly higher levels of water vapor begin to pass through the breathable barrier. The increased levels of water vapor passing through the outer cover can form condensate on the outer portion of the garment. The condensate is simply water but can be perceived as leakage. In addition, the condensate can create a damp uncomfortable feel to the outer portion of the garment which is unpleasant for those handling the article. Providing a breathable barrier which has a lower WVTR in such regions, while providing good breathability in the remaining regions, would provide a garment with excellent wearer comfort yet which limits the potential for outer cover dampness. In this regard, as discussed in greater detail herein below, segments having relatively high and low breathability can be strategically positioned within absorbent articles to help reduce and/or eliminate outer cover dampness. In a further aspect, the present invention provides films having stretch and recovery in the CD direction thereby providing a film and/or article incorporating the same, with excellent body conformance attributes. Moreover, excellent body conformance can be achieved without significant loss of breathability or loss of barrier properties.

Personal care articles generally include a liquid permeable topsheet, which faces the wearer, and a liquid-impermeable bottom sheet or outer cover. Disposed between the topsheet and outer cover is an absorbent core. Often the topsheet and outer cover are sealed to encase the absorbent core. The multi-segmented films and film laminates of the present invention are particularly well suited for use as an outer cover of a personal care article. Exemplary personal care articles are described, by way of examples only, in the following references: U.S. Pat. No. 5,415,644 to Enloe et al.; U.S. Pat. No. 4,798,603 to Meyer et al.; U.S. Pat. No. 5,810,797 to Menard et al.; U.S. Pat. No. 4,641,381 to Herren et al.; U.S. Pat. No. 4,701,175 to Boland et al.; and U.S. Pat. No. 4,938,797 to Van Gompel et al.; the entire content of the aforesaid references are incorporated herein by reference. In addition, although the following detailed description is made in the context of a disposable diaper, one skilled in the art will appreciate that the concepts of the present invention would also be suitable for use in connection with other types of absorbent articles, particularly other personal care products. In addition, although the present invention is described in the context of several specific configurations, it will be appreciated that further combinations or alterations of the specific configurations discussed below may be made by one skilled in the art without departing from the spirit and scope of the present invention.

Figure 9:
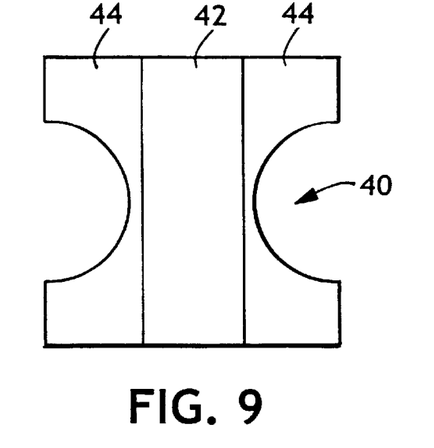
FIG. 9 is a top, plan view of a baffle for an absorbent article comprising a multi-segmented film of the present invention.

In reference to FIG. 9, a liquid impervious baffle for a diaper or incontinence garment is shown comprising a continuous multi-segmented film 40 comprising first segments 44 and second segment 42. First segments 44 can comprise a breathable film and second segment 42 can comprise a film having a reduced or lower WVTR relative to that of first segments 44. In a particular embodiment, first segments 42 can comprise a microporous LLDPE film and second segment 42 can comprise an opaque, non-breathable or less breathable elastic polyolefin film. Second segment 42 can either be elastic or inelastic. Further, in a preferred embodiment, first segment 44 can comprise a breathable, elastic monolithic film such as polyether ester or polyurethane. As indicated above such monolithic films can have good breathability where the polymer allows water vapor to readily diffuse through the film. By utilizing a low WVTR segment positioned along the central portion of the article the propensity of the article to develop outer cover dampness is reduced. Additionally and/or alternatively, utilization of a central elastic segment provides an article with improved body conformance.

Figure 10:
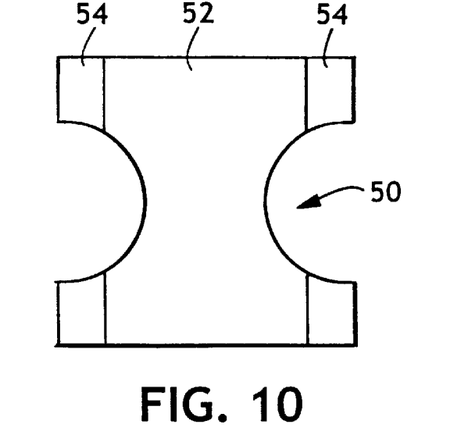
FIG. 10 is a top, plan view of a baffle for an absorbent article comprising a multi-segmented film of the present invention.
Figure 11:
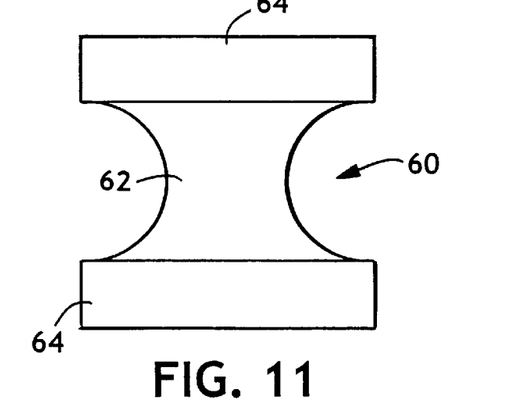
FIG. 11 is a top, plan view of a baffle for an absorbent article comprising a multi-segmented film of the present invention.

As a further example and in reference to FIG. 10, a liquid impervious baffle for a diaper or incontinence garment is shown comprising a continuous multi-segmented film 50 comprising first segments 52 and second segments 54. The baffle can be converted from the multi-segmented film 50 wherein the "ears" of the diaper correspond with second regions 54 and the central portion of the article corresponds to one or more first segments 52. First segment 52 desirably comprises a breathable film, such as for example a monolithic or multi-layered microporous film which can be elastic or inelastic. Second segments 54 desirably comprise an elastic segment with excellent stretch and recovery properties, such as for example, film segments comprising elastic polyurethane or KRATON/polyolefin blends. In a further example and in reference to FIG. 11, the multi-segmented film 60 can be converted such that the segments run across the width of the article as opposed to the length of the article as in FIG. 10. Multi-segmented film 60 can comprise first region 62 and second regions 64. First region 62 desirably comprises a breathable film and second regions 64 can comprise an elastic film. Second segments 64 can be breathable or non-breathable films. However, it will be appreciated by those skilled in the art that the WVTR of the ears and/or upper regions of the article may be increased such as by aperturing these regions.

Figure 12:
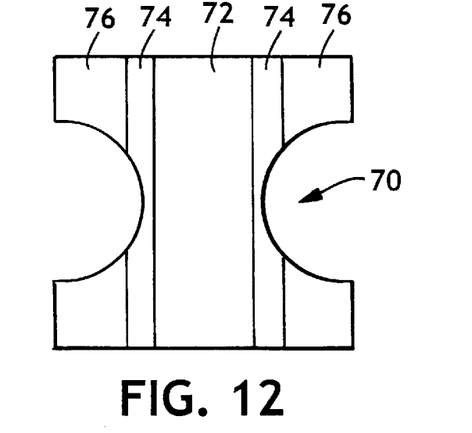
FIG. 12 is a top, plan view of a baffle for an absorbent article comprising a multi-segmented film of the present invention.
Figure 13:
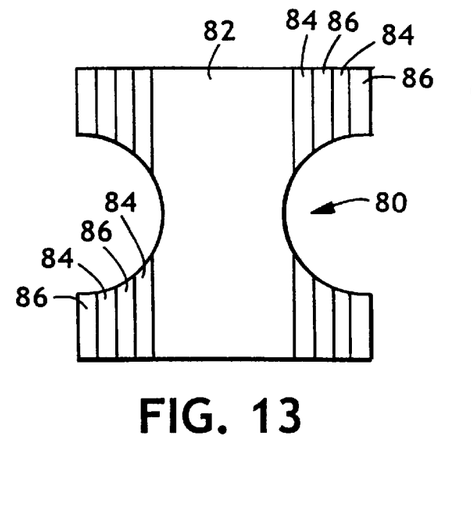
FIG. 13 is a top, plan view of a baffle for an absorbent article comprising a multi-segmented film of the present invention.

As a further example and in reference to FIG. 12, a liquid impervious baffle for a diaper or incontinence garment is shown comprising a continuous multi-segmented film 70 comprising first segment 72, second segments 74 and third segments 76. First segment 72 desirably comprises a breathable film which can be elastic or inelastic. In one embodiment, third segments 76 can comprise a breathable film and can be identical to or different from that of first segment 72; desirably third segments comprise an elastic breathable film. Second segments 74 can comprise an elastic film and/or a compatibilizing segment. As a particular example, first region 72 can comprise a filled microporous LLDPE film, second regions 74 can comprise a compatibilizing polypropylene impact copolymer and third segments 76 can comprise an elastic polypropylene. As indicated above, the ears or upper regions of the article non-adjacent the absorbent core can be apertured in order to increase the WVTR in those areas. As yet a further example and in reference to FIG. 13, multi-segmented film 80 can comprise first film segment 82, second film segments 84 and third film segment 86. First film segment 82 desirably comprises a breathable film such as those discussed above. In one embodiment, second film segment 84 can comprise a compatibilizing segment and third regions elastic segments. In a further embodiment, second film segment 84 can comprise an elastic segment and third segments 86 can comprise breathable films which can, optionally, comprise a composition similar to that of first segment 82. As a specific example, first segment 82 can comprise a LLDPE microporous film, second segments can comprise elastic polyethylene and third segments can likewise comprise a LLDPE microporous film.

Figure 14:
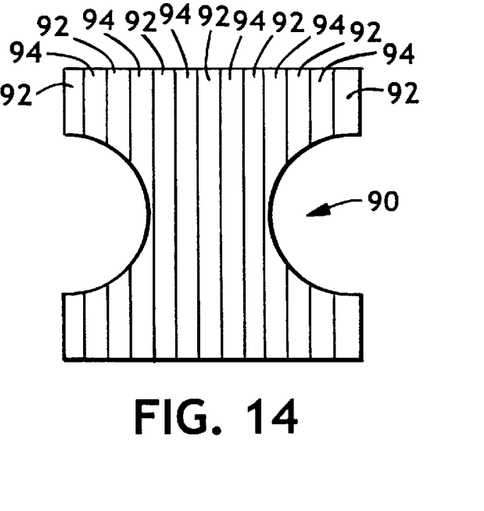
FIG. 14 is a top, plan view of a baffle for an absorbent article comprising a multi-segmented film of the present invention.

As a further example and in reference to FIG. 14, multi-segmented film 90 can comprise a plurality of first segments 92 separating a plurality of second segments 94. The multiple segments can comprise narrow segments, relative to the overall width of the film and/or article, which alternate over the entire width of the article. In a particular embodiment, first segments 92 can comprise an opaque breathable microporous LLDPE film having a $CaCO_3$ filler and second segments 94 can comprise an opaque, non-breathable LLDPE film having a $TiO_2$ filler. In an alternate embodiment, first segments 92 can comprise a breathable, microporous LLDPE film and second segments can comprise a breathable filled microporous elastic polyethylene film.

Figure 15:
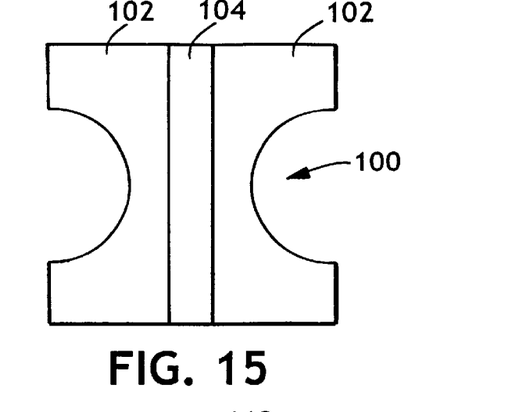
FIG. 15 is a top, plan view of a baffle for an absorbent article comprising a multi-segmented film of the present invention.

As a further example and in reference to FIG. 15, a liquid impervious baffle for a diaper or incontinence garment is shown comprising a continuous multi-segmented film 100 comprising first segments 102 and second segments 104. First segments 102 can comprise an opaque breathable film such as, for example, a filled microporous film. Second segment 104 can comprise a translucent and/or substantially transparent film. Positioning second segment 104 adjacent the absorbent core, such as down the central portion of the article, allows a parent or care giver to determine whether the diaper is soiled without removing the diaper. As a particular example, the translucent segment 104 can comprise an unfilled polyolefin film segment. This particular configuration could likewise be utilized in conjunction various other multi-segmented film embodiments including, but not limited, to those described herein above.

Figure 16:
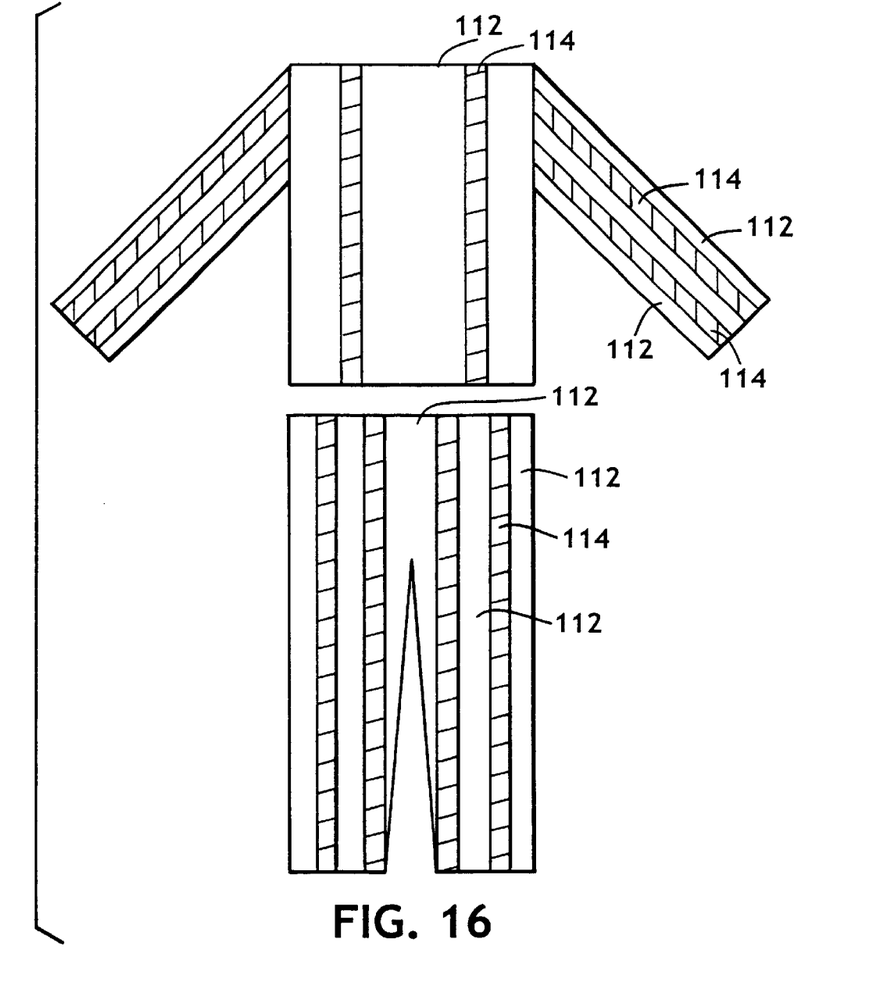
FIG. 16 is a front, flatwise view of a protective garment comprising a multi-segmented film of the present invention.
Figure 17:
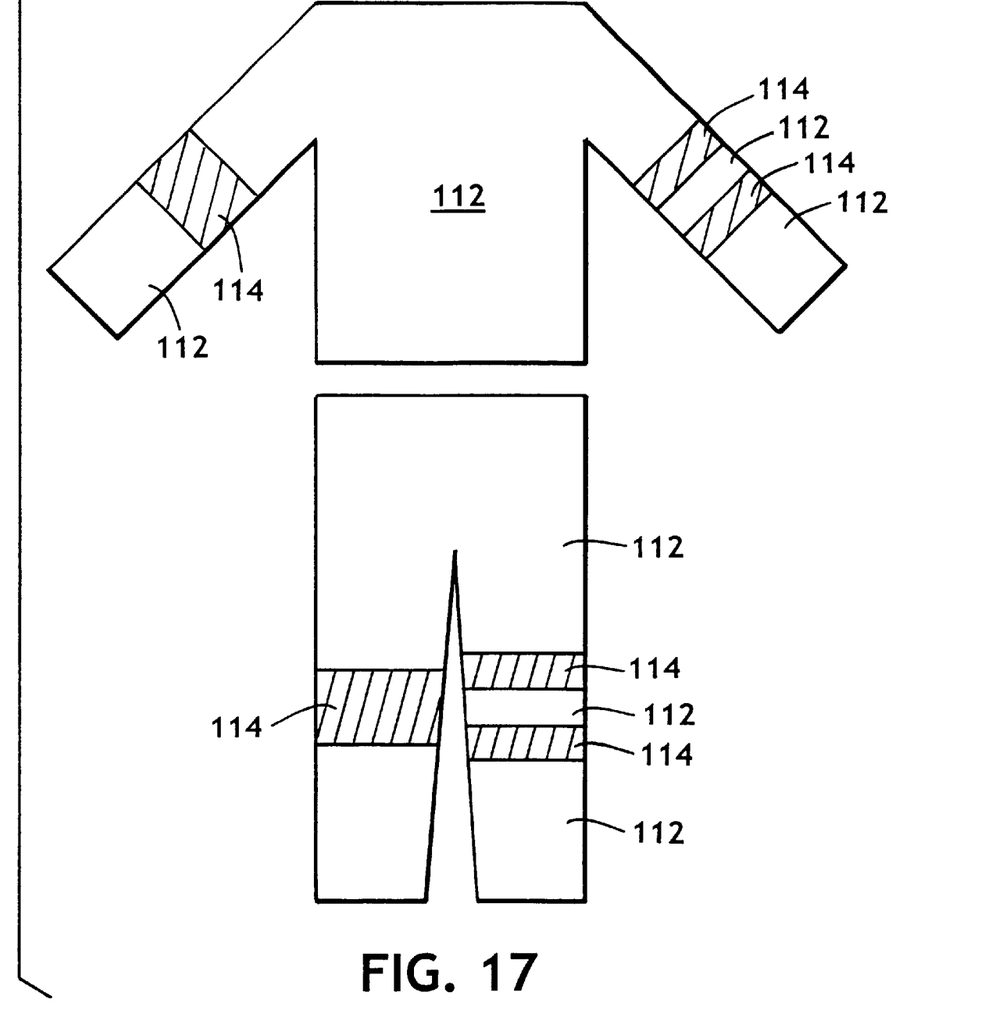
FIG. 17 is a front, flatwise view of a protective garment comprising a multi-segmented film of the present invention.

Multi-segmented films and/or laminates thereof may likewise be converted into surgical gowns, protective workwear and the like. In this regard, medical apparel is often required to provide a higher degree of protection to the wearer such as, for example, preventing penetration of blood (ASTM Test F 1670-97) and/or blood-borne pathogens (ASTM Test F 1671-97a). By comprising a continuous film, good stretch and body conformance can be achieved without loss of the desired barrier properties. In reference to FIGS. 16 and 17, surgical gowns or workwear can comprise breathable first segments 112 having excellent WVTRs and provide a garment that is comfortable to wear. Second segments 114 can comprise elastic segments and provide the garment with additional improved stretch and body conformance attributes. Desirably, second segments 114 comprise elastic, breathable films. Additionally, elastic second segments 114 can be strategically located as desired within the garment such as, for example, about or adjacent the joints.

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention.

Tests

Basis Weight: the basis weights of various materials can be determined in accordance with Federal Test Method No. 191A/5041.

Hydrohead: the hydrohead value is measure of the liquid barrier properties of a fabric and the hydrohead test determines the height of water or amount of water pressure (in millibars) that the fabric will support before liquid passes therethrough. A fabric with a higher hydrohead reading indicates it has a greater barrier to liquid penetration than a fabric with a lower hydrohead. The hydrohead can be performed according to Federal Test Standard 191A, Method 5514. Hydrohead data can also be obtained using a test similar to the aforesaid Federal Test Standard except modified as noted below. The hydrohead can also be determined using a hydrostatic head tester available from Marl Enterprises, Inc. of Concord, N.C. The specimen is subjected to a standardized water pressure, increased at a constant rate until the first sign of leakage appears on the surface of the fabric in three separate areas. (Leakage at the edge, adjacent clamps is ignored.) Thin fabrics and/or materials, such as a thin film, are supported to prevent premature rupture of the specimen.

WVTR: The water vapor transmission rate (WVTR) for the sample materials was calculated in accordance with ASTM Standard E96-80. Circular samples measuring three inches in diameter were cut from each of the test materials and a control which was a piece of CELGARD 2500 film from Hoechst Celanese Corporation of Sommerville, N.J. CELGARD 2500 film is a microporous polypropylene film. Three samples were prepared for each material. The test cups were number 68-1 Vapometer cups distributed by Thwing-Albert Instrument Company of Philadelphia, Pa. One hundred milliliters of water were poured into each vapometer cup and individual samples of the test materials and control material were placed across the open tops of the individual pans. The vapometer cups were mechanically sealed along the edges of the cup, leaving the associated test material or control material exposed to the ambient atmosphere over a 6.8 centimeter diameter circle having an exposed area of approximately 33.17 square centimeters. The cups were placed in a convection type oven at 100° F. (37.7° C.) for 24 hours. The oven was a constant temperature oven with external air circulating through it to prevent water vapor accumulation inside. After 24 hours, the pans were removed from the oven and weighed again. The preliminary test water vapor transmission rate values were calculated with Equation (I) below:

Test WVTR=(grams weight loss over 24 hours)×315.5 g/m$^2$/24 hours (I)

The relative humidity within the oven was not specifically controlled. Under the predetermined set conditions of 100° F. (37.7° C.) and ambient relative humidity, the WVTR for the CELGARD 2500 control has been defined to be 5000 grams per square meter for 24 hours. Accordingly, the control sample was run with each test and the preliminary test values were corrected to set conditions using Equation (II) below:

Standardized WVTR=(Test WVTR/control WVTR)×(5000 g/m$^2$/24 hours). (II)

It may be desirable to determine WVTRs in excess of about 3000 g/m$^2$/day using other testing systems such as, for example, the PERMATRAN-W 100K water vapor permeation analysis system, commercially available from Modern Controls, Inc. (MOCON) of Minneapolis, Minn.

Elasticity: The hysteresis and retraction/extension percent of individual film segments can be evaluated using standard testing equipment such as a SinTech Synergie 200 (TestWorks 3.1 software) using a 1 cm (wide) specimen with a gap length of 1 mm (i.e. the distance between the testing equipment jaws), a cross-head speed of 7.0 mm/minute and a load cell value of 50 lb. The sample is placed within the testing equipment jaws such that only the film segment of interest is located between the jaws. The specimen is elongated 100% of the original unbiased gap length (to 2 mm) and the jaws are then returned to the original gap length. The load exerted by the specimen is recorded during the cycling of the specimen. The average of five samples is used to calculate the particular values. The retraction/extension percent is calculated using the load at 50% elongation (1.5 mm) and can be calculated as follows:

$$\text{Retraction/Extension Percent} = \frac{\text{Load at 1.5 mm During Retraction}}{\text{Load at 1.5 mm During Extension}} \times 100$$

Hysteresis of a film segment can be calculated using the "Energy of Extension" and "Energy of Retraction" where the Energy of Extension is the area under the load/elongation curve for the sample going to 100% elongation (2 mm) and Energy of Retraction is the area under the load/elongation curve going from 100% elongation back to the original gap length (1 mm). The load/elongation curve is plotted as load vs. Elongation in the cycling of the sample described above. Thus, % hysteresis can be calculated as follows:

$$\text{Percent Hysteresis} = \frac{\text{Energy of Extension} - \text{Energy of Retraction}}{\text{Energy of Extension}} \times 100$$

We claim:

1. A multi-segmented film comprising:
   a unitary film having a machine-direction and a cross-direction and comprising a first film segment and a second film segment wherein said first and second film segments extend adjacent one another in at least one direction of said unitary film;
   said first film segment comprises a thermoplastic polymer and has a WVTR of at least 800 g/m$^2$/24 hours and wherein said first film segment comprises a first film composition:
   said second film segment comprises a thermoplastic polymer and has a WVTR less than that of the first film segment and wherein said second film segment comprises a second film composition; and
   said second film composition is different from said first film composition.

2. The multi-segmented film of claim 1 wherein said first film segment comprises a microporous film and wherein said multi-segmented film has a hydrohead of at least about 50 mbars.

3. The multi-segmented film of claim 2 wherein said first film composition comprises thermoplastic polymer and filler and further wherein said filler is distributed throughout said first film segment.

4. The multi-segmented film of claim 3 wherein said first film segment has micropores adjacent said filler.

5. The multi-segmented film of claim 4 wherein said first film segment has a WVTR in excess of 1500 g/m$^2$/24 hours and wherein said second film composition comprises thermoplastic polymer and filler and further wherein said filler is distributed throughout said second film segment.

6. The multi-segmented film of claim 5 wherein said second film segment comprises a microporous film having micropores adjacent said filler.

7. The multi-segmented film of claim 5 wherein said second film composition comprises a polyolefin elastomer.

8. The multi-segmented film of claim 7 wherein said first film composition comprises an inelastic polyolefin polymer.

9. The multi-segmented film of claim 8 wherein said first film segment comprises linear low density polyethylene and wherein said second film segment comprises an ethylene elastomer.

10. The multi-segmented film of claim 7 wherein said first film segment and second film segment comprise multilayer films and further wherein said multi-segmented film has a substantially uniform thickness.

11. The multi-segmented film of claim 6 wherein said first film segment has a higher weight percent filler than said second film segment.

12. A personal care article comprising (i) a liquid pervious topsheet; (ii) a liquid impervious outer cover comprising the multi-segmented film of claim 7; and (iii) an absorbent core positioned between said outer cover and said topsheet.

13. A personal care article comprising (i) a liquid pervious topsheet; (ii) a liquid impervious outer cover comprising the multi-segmented film of claim 9; and (iii) an absorbent core positioned between said outer cover and said topsheet.

14. The multi-segmented film of claim 4 wherein said second film segment comprises a non-microporous film and further wherein said second film composition comprises an elastic polymer.

15. The multi-segmented film of claim 14 wherein said second segment comprises an elastic polymer selected from the group consisting of polyurethanes, polyesters, polyamides, vinyl acetates, acrylates and blends thereof.

16. A multilayer laminate comprising the multi-segmented film of claim 4 and a sheet fixedly attached to a first surface of said multi-segmented film.

17. The multilayer laminate of claim 16 wherein said sheet comprises a nonwoven web.

18. A personal care article comprising (i) a liquid pervious topsheet; (ii) a liquid impervious outer cover comprising the multilayer laminate of claim 17; and (iii) an absorbent core positioned between said outer cover and said topsheet.

19. A surgical gown comprising the laminate of claim 17.

20. The multilayer laminate of claim 16 wherein said sheet comprises an extensible fabric and wherein said second film composition comprises an elastomer.

21. The multi-segmented film of claim 4 wherein said multi-segmented film has a substantially uniform thickness and further wherein said first and second segments extend adjacent one another in the machine-direction.

22. A multilayer laminate comprising the multi-segmented film of claim 1 and a sheet fixedly attached to a surface of said multi-segmented film.

23. The multilayer laminate of claim 22 wherein said sheet comprises a nonwoven web.

24. A personal care article comprising (i) a liquid pervious topsheet; (ii) a liquid impervious outer cover comprising the multi-segmented film of claim 1; and (iii) an absorbent core positioned between said outer cover and said topsheet.

25. A surgical gown comprising the multi-segmented film of claim 1.

26. A multi-segmented film comprising:
a unitary film having a machine-direction and a cross-direction and comprising a first film segment and a second film segment wherein said first and second film segments extend in the machine-direction of said unitary film and further wherein said unitary film has a hydrohead of at least 50 mbars;
said first film segment comprises a first thermoplastic polymer and said second film segment comprises a second thermoplastic polymer and wherein said first thermoplastic polymer is different from said second thermoplastic polymer; and
wherein said first film segment comprises a microporous film and has a WVTR of at least 1500 $g/m^2/24$ hours and further wherein said second film segment comprises an elastomer.

27. The multi-segmented film of claim 26 wherein said first film segment comprises an inelastic polymer and said second film segment comprises a non-porous film segment and comprises a polyolefin elastomer.

28. The multi-segmented film of claim 26 wherein said first film segment comprises an inelastic polymer and said second film segment comprises an elastic polymer selected from the group consisting of polyurethanes, polyesters, polyamides, vinyl acetates, acrylates and blends thereof.

29. The multi-segment film of claim 26 wherein said first film segment comprises an inelastic polyolefin polymer and a filler and wherein said filler is distributed throughout said first film segment and micropores are adjacent said filler and further wherein said second film segment comprises an elastomer.

30. The multi-segmented film of claim 29 wherein said second film segment comprises a polyolefin elastomer and further comprises an opacifying filler.

31. A multilayer laminate comprising the multi-segmented film of claim 26 and a sheet fixedly attached to a first surface of said multi-segmented film.

32. The multilayer laminate of claim 31 wherein said sheet comprises a nonwoven web.

33. The multilayer laminate of claim 31 wherein said sheet comprises an extensible fabric.

34. A personal care article comprising (i) a liquid pervious topsheet; (ii) a liquid impervious outer cover comprising the multilayer laminate of claim 33; and (iii) an absorbent core positioned between said outer cover and said topsheet.

35. A personal care article comprising (i) a liquid pervious topsheet; (ii) a liquid impervious outer cover comprising the multi-segmented film of claim 26; and (iii) an absorbent core positioned between said outer cover and said topsheet.

36. A surgical gown comprising the multi-segmented film of claim 26.

* * * * *